US012766225B2

(12) United States Patent
Gain et al.

(10) Patent No.: US 12,766,225 B2
(45) Date of Patent: Oct. 20, 2026

(54) METHOD FOR PREPARING AN ALLOGRAFT OR XENOGRAFT MATERIAL FROM A CRYSTALLINE LENS CAPSULE

(71) Applicants: UNIVERSITE JEAN MONNET SAINT ETIENNE, Saint Etienne (FR); CENTRE HOSPITALIER UNIVERSITAIRE, Saint Etienne (FR)

(72) Inventors: Philippe Gain, Lyons (FR); Gilles Thuret, St Bonnet les Oules (FR); Zhiguo He, Saint Etienne (FR)

(73) Assignees: UNIVERSITE JEAN MONNET SAINT ETIENNE, Saint Etienne (FR); CENTRE HOSPITALIER UNIVERSITAIRE, Saint Etienne (FR)

( * ) Notice: Subject to any disclaimer, the term of this patent is extended or adjusted under 35 U.S.C. 154(b) by 1178 days.

(21) Appl. No.: 17/629,275

(22) PCT Filed: Jul. 22, 2020

(86) PCT No.: PCT/EP2020/070692
§ 371 (c)(1),
(2) Date: Jan. 21, 2022

(87) PCT Pub. No.: WO2021/013893
PCT Pub. Date: Jan. 28, 2021

(65) Prior Publication Data

US 2022/0241463 A1 Aug. 4, 2022

(30) Foreign Application Priority Data

Jul. 22, 2019 (FR) ...................................... 1908275

(51) Int. Cl.
*A61L 27/36* (2006.01)
*C12N 5/079* (2010.01)

(52) U.S. Cl.
CPC ....... *A61L 27/3691* (2013.01); *A61L 27/3604* (2013.01); *C12N 5/0621* (2013.01); *A61L 2420/02* (2013.01); *A61L 2430/16* (2013.01); *A61L 2430/40* (2013.01); *C12N 2533/52* (2013.01); *C12N 2533/90* (2013.01)

(58) Field of Classification Search
None
See application file for complete search history.

(56) References Cited

U.S. PATENT DOCUMENTS

2002/0183844 A1* 12/2002 Fishman ............. A61L 27/3604
623/4.1
2017/0027754 A1 2/2017 Muller
2017/0319329 A1 11/2017 Muller et al.
2019/0038399 A1 2/2019 Muller

FOREIGN PATENT DOCUMENTS

EP 1007623 B1 10/2005
FR 3083978 A1 1/2020
WO 2014/140434 A1 9/2014
WO 2018/102329 A1 6/2018

OTHER PUBLICATIONS

Damgaard et al., “Biological Lenticule Implantation for Correction of Hyperopia: An Ex Vivo Study in Human Comneas”, Journal of Refractive Surgery, vol. 34, No. 4, 2018, pp. 245-252.
Galal et al., “Human Anterior Lens Capsule as a Biologic Substrate for the Ex Vivo Expansion of Limbal Stem Cells in Ocular Surface Reconstruction”, Cornea, vol. 26, No. 4, May 2007, pp. 473-478.
Hartmann et al., “Human and porcine anterior lens capsule as support for growing and grafting retinal pigment epithelium and iris pigment epithelium”, Graefe’s Arch Clin Ophthalmol (1999), 237: pp. 940-945.
Kopsachilis et al., “Descemet’s membrane substrate from human donor lens anterior capsule”, Clinical and Experimental Ophthalmology 2012; 40, pp. 187-194.
Nicolini et al., “The anterior lens capsule used as support material in RPE cell-transplantation”, Acta Ophtalmol. Scand. 2000: 78: 527-531.
Spinozzi et al., “Evaluation of the Suitability of Biocompatible Carriers as Artificial Transplants Using Cultured Porcine Corneal Endothelial Cells”, Current Eye Research, https://doi.org/10.1080/02713683.2018.1536215.
Van den Bogerd et al., “Characterizing human decellularized crystalline lens capsules as a scaffold for corneal endothelial tissue engineering”, Journal of Tissue Engineering and Regenerative Medecine, Dec. 2017; 1-9.
Yoeruek et al., “Human Anterior Lens Capsule as Carrier Matrix for Cultivated Human Corneal Endothelial Cells”, Cornea, vol. 28, No. 4, May 2009, pp. 416-420.
English abstract provided for FR3083978A1.

* cited by examiner

*Primary Examiner* — Michael V Meller
(74) *Attorney, Agent, or Firm* — BCF LLP

(57) ABSTRACT

The invention concerns a process for preparing an allograft or xenograft material from a lens capsule, wherein the process comprises the following steps:

Decellularizing (200) a lens capsule to obtain a decellularized lens capsule, Depositing (300) the decellularized capsule on a microporous support membrane to obtain a stack composed of the decellularized lens capsule and the support membrane, Lyophilizing (400) the stack to obtain a lyophilized stack, Sterilizing (500) the lyophilized stack to obtain a sterilized stack, Packaging (600) the sterilized stack to obtain allograft or xenograft materials.

13 Claims, 6 Drawing Sheets

METHOD FOR PREPARING AN ALLOGRAFT OR XENOGRAFT MATERIAL FROM A CRYSTALLINE LENS CAPSULE

CROSS-REFERENCE TO RELATED APPLICATIONS

This application is a national phase filing under 35 U.S.C. § 371 of International Application No. PCT/EP2020/070692 filed on Jul. 22, 2020, which claims benefit of priority from French Patent Application No. 1908275 filed Jul. 22, 2019, the contents of which are hereby incorporated by reference in their entirety.

FIELD OF THE INVENTION

The present invention relates to the general technical field of producing an implantable human or animal graft for ophthalmological applications.

To be more precise, the invention relates to a process for preparing a sterile, lyophilized, membrane-forming allograft or xenograft material from a lens capsule.

This allograft or xenograft material is suitable for use as a graft in ocular surgery, in particular in the context of corneal and/or retinal surgery.

BACKGROUND OF THE INVENTION

The lens capsule is a transparent, resistant membrane that envelops the lens.

At present, lens capsules are considered surgical waste. In particular, during cataract surgery, a disk of anterior lens capsule (hereinafter referred to as “anterior capsule”) is cut out, for example using mechanized cutting instruments (such as a femtosecond laser, or any other cutting instrument known to the person skilled in the art). This anterior capsule disk—with a diameter substantially equal to 6 millimeters—constitutes surgical waste that is systematically destroyed.

However, the lens capsule, which is chiefly composed of collagen IV, is an excellent support for culturing different cell types useful for producing cell and tissue therapy materials such as corneal endothelial or corneal epithelial grafts or retinal grafts (pigmented epithelium, photoreceptors, etc.).

Anterior capsules from cataract surgery (850 000 operations per year in France, of which at least 10% are performed using a mechanized cutting instrument to cut the anterior capsule) could be used to make allograft or xenograft materials.

Another source of lens capsule supply concerns tissue and organ donations, in particular corneas or whole globes, for which anterior and posterior lens capsule disks could be cut from previously removed lens capsules, this supply solution allowing larger diameter disks (between 7 and 11 millimeters) to be cut and both the anterior and posterior lens capsules to be recovered.

Document US 2002/183844 relates to a microfabricated substrate tissue for pigment epithelium transplantation and the manufacturing process for same. The process comprises the steps consisting in modifying a membranous tissue and growing cells on the modified membranous tissue. The process described in US 2002/183844 allows the membranous tissue to be modified in order to promote cell adhesion thereto.

No industrial process for preparing an allograft or xenograft material from a cut lens capsule, for example cut with mechanized cutting instruments (such as an ultrafast laser), or any other electrical or mechanical or manual cutting instrument has been proposed to date.

One aim of the present invention is to remedy this disadvantage.

BRIEF DESCRIPTION OF THE INVENTION

To this end, the invention provides a process for preparing an allograft or xenograft material from a lens capsule, remarkable in that the process comprises the following steps:

- Decellularizing a lens capsule to obtain a decellularized lens capsule,
- Depositing the decellularized capsule on a microporous support membrane to obtain a stack composed of the decellularized lens capsule and the support membrane,
- Lyophilizing the stack to obtain a lyophilized stack,
- Sterilizing the lyophilized stack to obtain a sterilized stack,
- Packaging the sterilized stack to obtain allograft or xenograft materials.

Thus, and as illustrated in steps 610, 620 of FIG. 1, the process according to the invention provides, in a sterile container, an easy-to-handle decellularized capsule for the following types of ocular surgery:

- closure of a corneal endothelial defect: this is a method for treating a frequent corneal pathology called Fuchs' endothelial dystrophy, characterized by the presence of abnormal structures of Descemet's membrane located on the posterior face of the central cornea. The surgeon then mechanically removes this abnormal layer by a procedure called Descemetorhexis. Descemetorhexis leaves a defect in the endothelium that is slowly filled by endothelial cells that migrate from the periphery. In order to accelerate the migration of these cells, it is possible to cover the defect with a thin, transparent membrane that promotes cell adhesion and migration. The decellularized lens capsule has all these qualities.
- closure of a macular hole (MH): this frequent retinal pathology can benefit, after vitrectomy, from the placement of a decellularized lens capsule in order to facilitate the closure of the hole.

In both applications the decellularized capsule is used as is, without an additional recellularization step.

Alternatively, and as illustrated in steps 630 and 640 of FIG. 1, the sterilized decellularized capsule can be recellularized with corneal endothelial or epithelial cells, or cells from the pigmented retinal epithelium or other retinal cells such as photoreceptors, ganglion cells, etc., to obtain a recellularized graft, contained in a culture medium, ready for transplantation.

Preferred but non-limiting aspects of the process according to the invention are the following:

- the process may further comprise a step of cutting the lens capsule to form gripping means;
- the process may comprise, prior to the decellularization step:
  - a step of receiving a primary biological material selected from: a globe or a cornea from an organ donation, or a lens capsule from a cataract operation and constituting surgical waste,
  - if the biological material is a globe or cornea:
    - a step of extracting the lens,
    - a step of cutting the anterior and posterior lens capsules;
- the step of cutting the anterior and posterior lens capsules comprises the substeps consisting in:

inserting the entire lens into a holding device including a housing transparent to laser radiation, and suction means for pressing the lens into the housing,
cutting the anterior face of the lens capsule using laser radiation to obtain a cut anterior disk,
cutting the posterior face of the lens capsule using laser radiation to obtain a cut posterior disk,
dissecting the cut anterior and posterior disks to obtain an anterior and a posterior lens capsule;

the process may further comprise a step of marking the lens capsule to form orientation marker means, said marking step consisting of applying a biocompatible ink through the support membrane;

the decellularization step may comprise the following substeps consisting in:
immersing the lens capsule in a decellularizing liquid, and
optionally subjecting the immersed capsule to mechanical vibrations and/or mechanically scraping the surface of the lens capsule,
rinsing the lens capsule with a rinsing liquid (such as saline solution);

the deposition step may comprise the substeps consisting in:
positioning the lens capsule flat on the support membrane,
desiccating the lens capsule to promote adhesion of the lens capsule to the support membrane;

the process may also comprise, after the packaging step, a cell or tissue culture step, said culture step comprising the substeps consisting in:
coating the lens capsule with a substance that promotes the adhesion of the cells/tissues to be cultured,
growing cells/tissues on the lens capsule;

the process may also comprise, after the packaging step, a step of rehydrating the allograft or xenograft material, to allow the use of the lens capsule either directly as a healing agent, or after the implementation of a cell or tissue culture step.

The invention also relates to a surgical kit for treating ocular pathology, remarkable in that the kit comprises an allograft or xenograft material obtained by implementing the process described above.

BRIEF DESCRIPTION OF THE DRAWINGS

Other advantages and features of the process according to the invention will be emerge from the following description of several alternative embodiments, given by way of non-limiting examples, from the appended drawings wherein.

DETAILED DESCRIPTION OF THE INVENTION

Various examples of the process for preparing an allograft or xenograft material will now be described with reference to the figures. In these various figures, the equivalent elements are designated by the same numerical reference.

1. General Points

Figure 1:
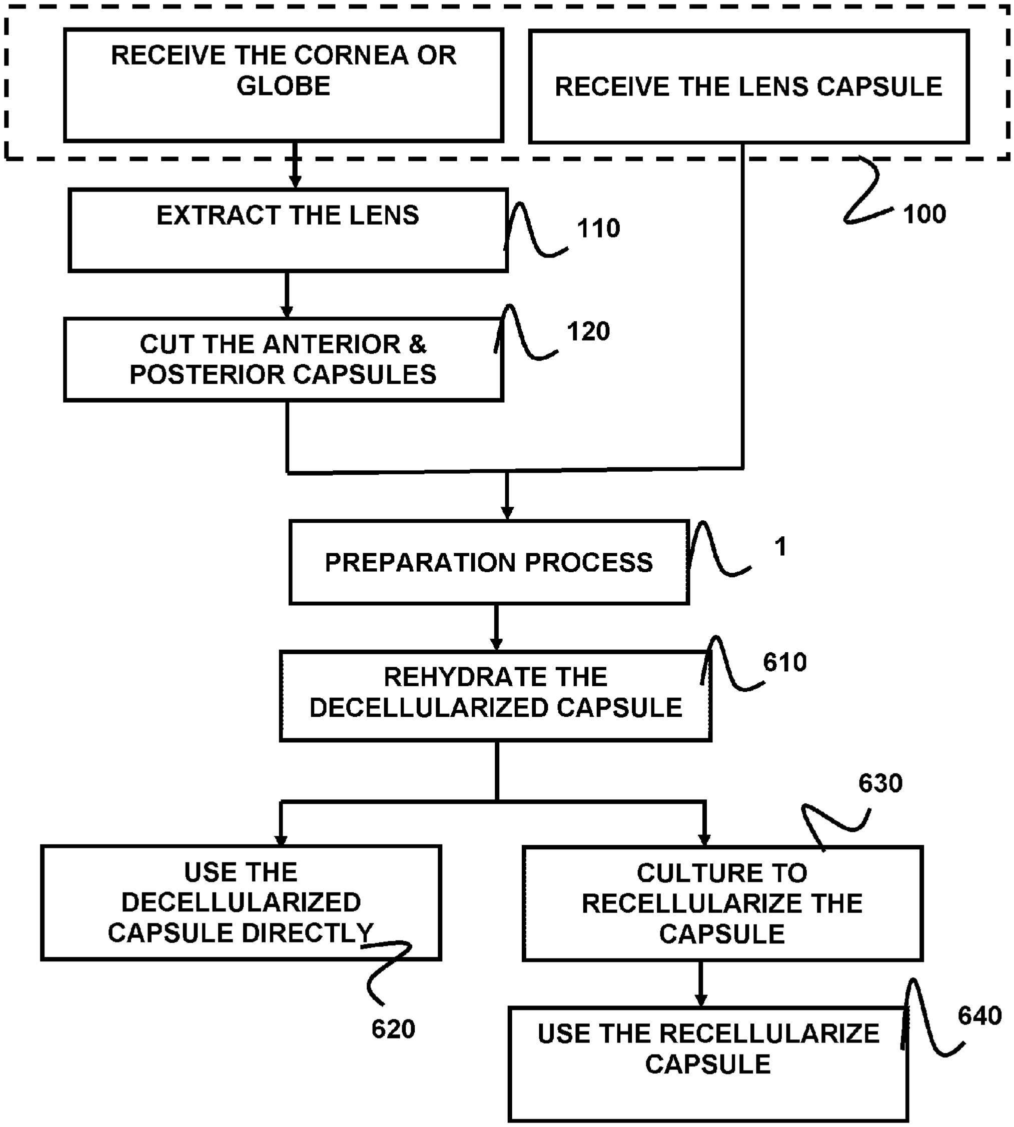
FIG. 1 is a schematic representation of:
the different possible sources of supply of lens capsules, as well as
the different possible uses of the lens capsules prepared by the preparation process according to the invention.
Figure 2:
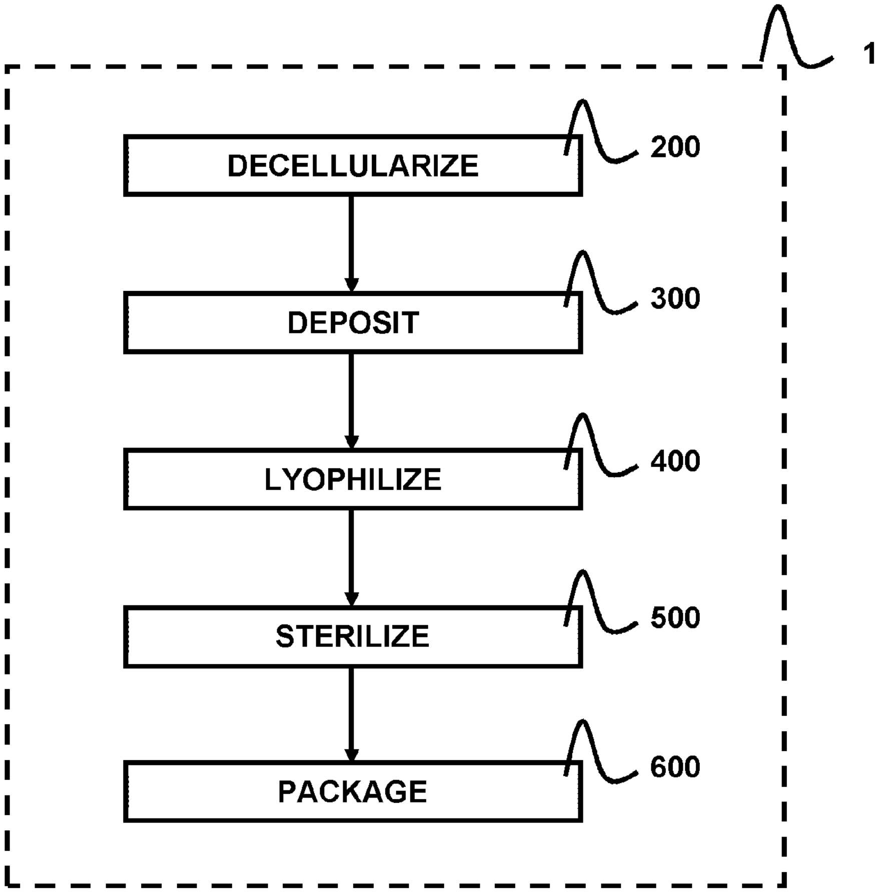
FIG. 2 is a schematic representation of the steps of the preparation process according to the invention.

With reference to FIG. 2, the process 1 comprises the following steps:
Decellularizing 200 each lens capsule to obtain decellularized lens capsules,
Depositing 300 each capsule flat on a synthetic support, for example a microporous cell culture insert membrane,
Lyophilizing 400 each lens capsule to obtain lyophilized lens capsules (lyophilization preferably being done directly with the synthetic support but also possible being done with the capsule alone),
Sterilizing 500 each lyophilized lens capsule to obtain sterilized lens capsules (thus with or without the synthetic support),
Packaging and storing 600 each sterilized lens capsule to obtain allograft or xenograft materials.

As will be described in greater detail in section 3 below, allograft or xenograft material thus obtained (i.e., decellularized, lyophilized, sterilized and packaged lens capsule) can be used for transplantation. To be more precise, the decellularized lens capsule can be used either:
Directly after the implementation of a rehydration step 610, or
After the implementation of a culture step 630.

2. Detailed Description of the Steps of the Preparation Process

2.1. Receiving Biological Material

The lens capsules prepared from the preparation process according to the invention may be derived from different sources of supply. In particular, these lens capsules may be derived from:
donations of corneas or globes, or from
lens capsules cut on cataract patients.

Depending on the source of supply, the preparation process may comprise steps prior to the decellularization step.

2.1.1. Cornea or Globe Donation

In the case of a cornea or globe donation, the anterior and posterior lens capsules are cut from whole lenses:
extracted during a corneal or globe removal from an organ donor patient (the lens being surgical waste from corneal or globe removal for therapeutic purposes)
stored in a sterile container including a preservation liquid—such as a surgical ocular perfusion liquid or any other sterile preservation medium known to the person skilled in the art—to facilitate their transport to a site for carrying out the process according to the invention.

Figure 3:
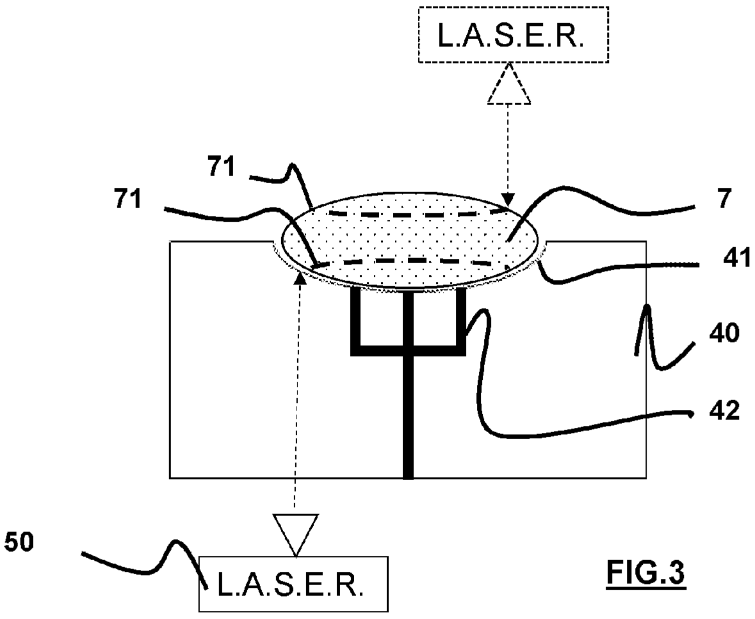
FIG. 3 is a schematic cross-section of a lens holding device.
Figure 4:
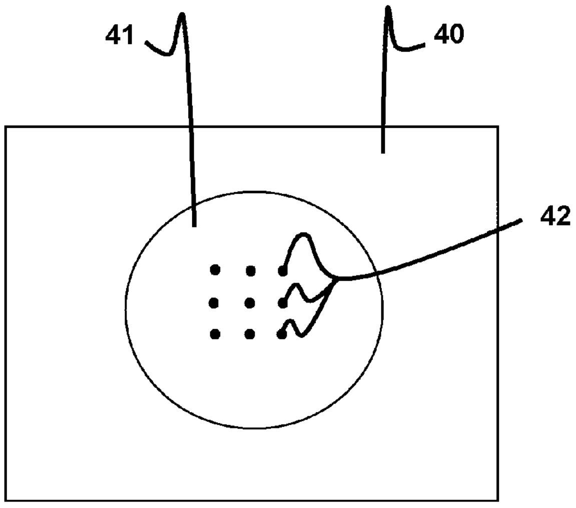
FIG. 4 is a schematic top-view of the lens holding device.

Once the lenses are made available at the process site, the anterior and posterior lens capsules are cut out using, for example:

- a lens holding device allowing the immobilization of the lens 7 during the cutting operations of the anterior and posterior lens capsules; such a holding device is illustrated in FIGS. 3 and 4; it comprises a support pad 40 transparent to laser radiation, the support pad 40 including:
  - a housing whose receiving wall 41 (i.e., wall intended to come into contact with the lens) is of a concave shape complementary to the shape of the lens 7,
  - one (or several) suction conduit(s) 42, one end of which opens into the receiving wall 41, the other end of the suction conduit being intended to be connected to a suction system (not shown) so as to generate a vacuum between the receiving wall 41 and the lens 7 in order to lock the lens in position,
- a cutting system 50 comprising an ultrafast (femtosecond, for example, but not only) laser source to cut the anterior and posterior lens capsules 71.

Alternatively, the anterior and posterior capsules can be cut using an automated or manual drill bit.

To be more precise, in the case of an organ donation, the process may comprise the following steps prior to the decellularization step 200:

- inserting the entire lens into a lens holding device comprising first and second faces transparent to laser radiation,
- cutting a disk of diameter comprised between 2 and 11 millimeters (or several small disks of small diameter) on the anterior face of the lens capsule to obtain one (or several) cut anterior disk(s),
- cutting a disk of diameter comprised between 2 and 11 millimeters (or several small disks of small diameter) on the posterior face of the lens capsule to obtain one (or several) cut posterior disk(s),
- dissecting the cut anterior and posterior disks to obtain an anterior and a posterior lens capsule,
- storing each lens capsule thus obtained in a sterile manner in a respective container including a preservation liquid (water, surgical eye perfusion liquid, etc.) prior to implementing the following steps of the process.

This regular source of supply makes it possible to cut lens capsules to obtain preferentially disks with a diameter greater than 6 millimeters. Moreover, for each given lens, it is possible to recover two lens capsules (anterior capsule and posterior capsule), which maximizes the quantity of biological material used to produce a cell and/or tissue therapy material, as this biological material is usually not used for therapeutic purposes.

Figure 5:
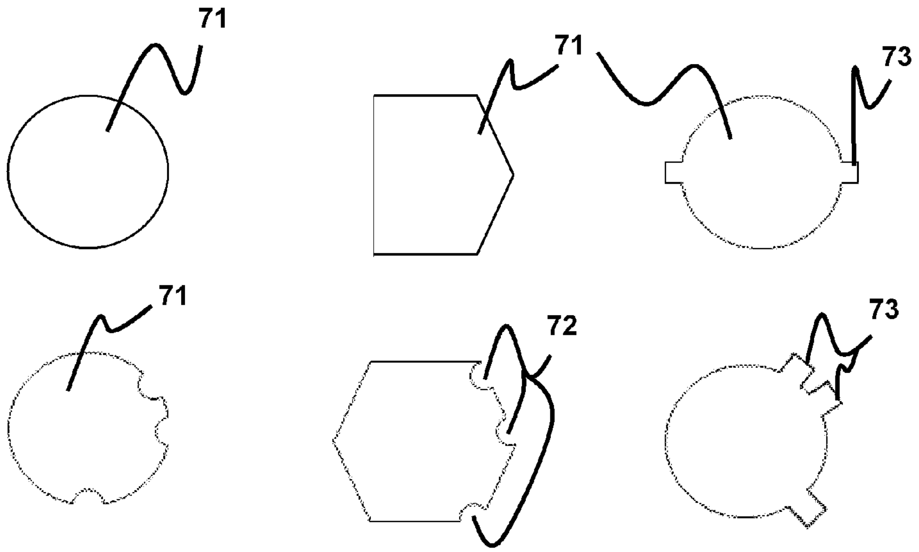
FIG. 5 is a schematic representation of different shapes of cut lens capsules.

Of course, and as illustrated in FIG. 5, the cut lens capsules may have shapes other than a disk. For example, each cut lens capsule may have a polygonal, pentagonal, square, triangular, etc., shape depending on the intended use.

Furthermore, each cut capsule may comprise orientation marker means 72—such as one (or several) notch(es)—to provide the practitioner with an indication of the orientation of the capsule 71 (i.e., front face of the capsule versus back face), in order to respect the natural curvature of the capsules that follow the biconvex shape of the lens and to know with certainty how to orient the graft in the eye; in particular in the case of a recellularized capsule graft, the orientation marker allows the practitioner to respect the correct orientation of the cells that are deposited on the concave face of the capsule (for the cornea, for example, the corneal endothelial cells must face the inside of the eye; for the retina, the pigmented epithelium cells must face the inside of the eye, etc.).

Each cut capsule may also comprise gripping means 73—such as one (or several) gripping lugs—to facilitate handling of the capsule. These gripping means 73 thus serve as a "jaw" during grafting to allow the practitioner to handle the capsule without damage when it is covered with cells.

Advantageously, the orientation marker means can be integrated to the gripping means.

2.1.2. Surgical Waste

In the case of lens capsules from cataract surgery patients, the anterior lens capsule (usually a 5 to 6 millimeter diameter disk) is cut by the practitioner under sterile conditions using a femtosecond laser source during the cataract surgery (or by an electric or mechanical cutting device called continuous circular capsulorhexis, or CCC).

Each cut lens capsule disk is packaged in a sterile container including a preservation liquid (such as water or surgical eye perfusion liquid, etc.) in order to send them to the site where the process according to the invention is implemented.

For these recovered and thus already cut capsules, the process can comprise, prior to the decellularization step, an additional cutting step (by mechanical drill or by laser) to make asymmetrical marks forming orientation markers and/or gripping means.

2.2. Decellularization

The decellularization step 200 removes residual epithelial cells and crystalline fibers attached to the lens capsule while maintaining the structure and conformation of the lens capsule. This decellularization reduces or eliminates the risk of an immune reaction in the patient transplanted with the allograft or xenograft material obtained by implementing the process according to the invention.

The decellularization step 200 provides a decellularized lens capsule which forms:

- a healing agent that can be used directly after rehydration (for endothelial defects or for macular holes), or
- a matrix base for subsequent cell and/or tissue culture.

The decellularization step 200 can implement different techniques known to the skilled person based in particular on chemical means (use of fluids suitable for decellularization), and/or on mechanical means (mechanical vibrations, shaking, scraping, etc.). As the cells to be removed are only on the surface of the capsule, the means of decellularization are simple (immersion in water and shaking may suffice for example).

For example, in an embodiment of the invention, the decellularization step 200 may comprise the following substeps:

- immersing the received lens capsule in a decellularizing liquid (including for example pure water which bursts the cells by osmotic shock, sodium chloride (NaCl), and/or ethylene diamine tetra acetic (EDTA), and/or a sodium dodecyl sulfate detergent and/or a DNase enzyme), and
- optionally subjecting the immersed capsule to mechanical vibrations and/or mechanically scraping the surface of the lens capsule, to remove any residual epithelial cells and/or lens fibers attached to the lens capsule,
- removing the lens capsule and rinsing it with a rinsing liquid (such as saline solution),
- optionally repeating the preceding substeps to obtain a decellularized lens capsule.

The implementation of the decellularization step 200 provides a decellularized lens capsule with good biocompatibility and biomechanical strength.

2.3. Step of Deposition on a Microporous Support Membrane

The step of depositing 300 the lens capsule on a microporous membrane 31 provides a flat stack including the membrane 31 and the capsule 71. Such a stack is easy to handle, ready to use for different purposes (i.e., ocular surgery, or cellular and tissue bioengineering).

Figure 6:
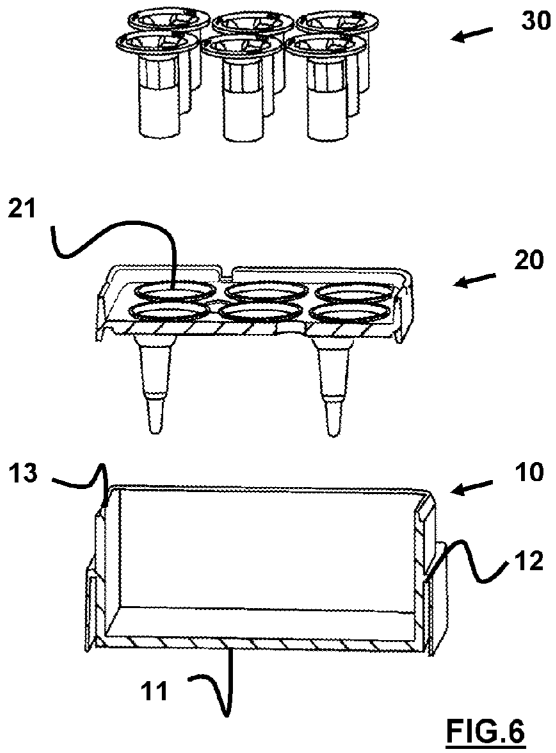
FIG. 6 is a schematic representation of different aspects of a cell culture device.
Figure 7:
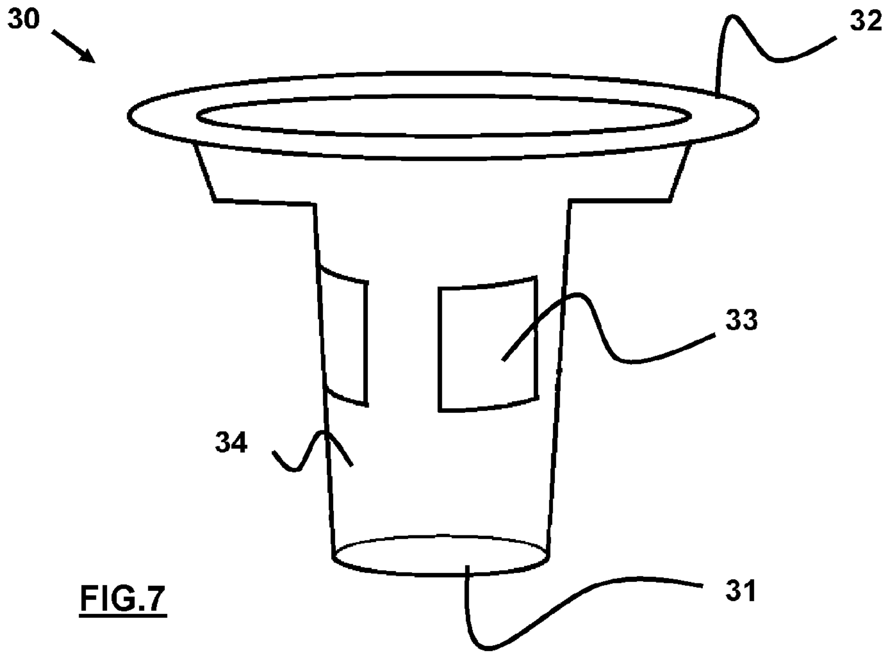
FIG. 7 is a schematic representation of a housing of the cell culture device.

The membrane 31 may be that of a cell culture insert as shown in FIGS. 6 and 7, or any other device having a microporous membrane, typically one suitable for cell cultures. The microporous membrane 31 serves as protection but also subsequently allows cells 74 to be cultured on the surface of the capsule 71 if necessary.

The membrane may be made of any material known to the skilled person for performing cell/tissue culture. The microporous membrane 31 may be an inorganic membrane, in particular an $Al_2O_3$, $TlO_2$ or $ZrO_2$ membrane although other inorganic materials such as pyrolytic carbon may be used. Alternatively, the membrane 31 may be an organic membrane, such as a polyvinylidene fluoride, polycarbonate (PC) or polyethylene terephthalate (PET) membrane.

The membrane 31 is semitransparent, allowing the capsule 71 to be easily seen through.

Figure 8:
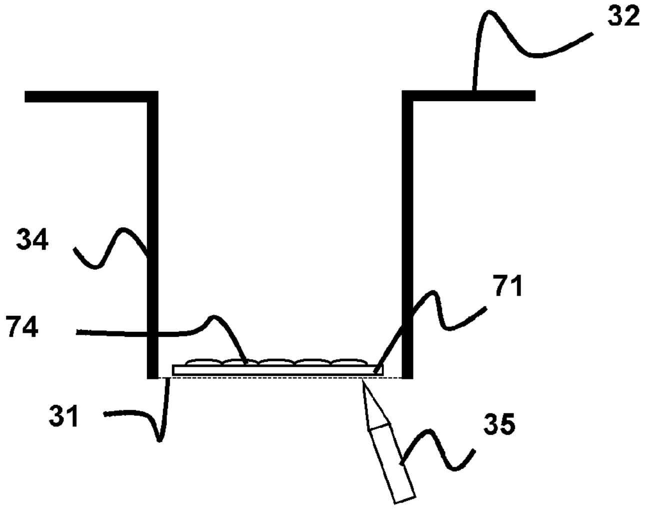
FIG. 8 is a schematic representation of a lens capsule marking step.

Advantageously, the porosity of the membrane 31 allows the capsule 71 to be marked to define one (or several) orientation marker means, for example with a biocompatible ink, through the membrane 31 and without having to directly touch the capsule 71. This is useful during bioengineering when the capsule 71 is covered with cells 74. A marking can then be made, for example with a surgical marker 35 with cresyl violet. This marking is preferably asymmetrical such as an asymmetrical letter F, S or such as 3 peripheral points (2 side by side, 1 distant), without directly touching/injuring the cells as illustrated in FIG. 8. Alternatively, the marking can be made indelibly in the material (for example by mechanical or laser microperforation or by femtosecond laser engraving, etc.).

Advantageously, the porosity of the membrane 31 also allows the capsule 71 to be stained with trypan blue or any other vital dye known to the skilled person, on its posterior face which does not contain any cells. This staining makes it easier to see the membrane when handled during introduction into the eye and then installation on the posterior face of the cornea or in front of a macular hole.

During the deposition step 300, the lens capsule is delicately deposited on the membrane to which it adheres spontaneously after a simple desiccation.

The lens capsule attached to the membrane forms a stack which can then be lyophilized, sterilized, stored and used for different applications.

As noted above, the membrane 31 may be integrated to a cell culture device known to the skilled person, such as the cell culture device described in WO2018/102329.

With reference to FIGS. 6 and 7, such a cell culture device may comprise:

- a parallelepipedic reservoir 10 for containing a cell or tissue culture medium, the reservoir 10 including a bottom 11 and four side walls 12 defining a top opening,
- a removable tray 20 intended to be positioned on the upper rim 13 of the reservoir 10, the tray 20 including a plurality of circular holes 21 each for receiving a respective housing 30,
- a plurality of housings 30 each including a membrane 31, each housing 30 being structured to fit through a respective circular hole 21 and extend below the tray 20 so that the membrane 31 of each housing 30 is immersed in the culture medium contained in the reservoir 10 when the removable tray 20 is positioned on the reservoir 10 and the housing 30 is inserted into its associated circular hole 21.

Specifically, housing 30 comprises:

- a top flange 32 intended to be rested on the edges of a respective hole 21 of the removable tray 20,
- a base attached to the bottom face of the flange 32, the base including at least one frustoconical side wall 33 that tapers in a direction away from the flange 32, the side wall 33 including one (or several) slots 34 to allow passage of the culture medium, and
- the membrane 31 attached to the free end of the side wall 33 and extending in a plane substantially parallel to a plane containing the top flange 32, the membrane 31 including a top face and an opposite bottom face, the top face being closer to the top flange than the bottom face.

The membrane 31 may be removable. In this case, at the end of the deposition step 300, a stack is obtained consisting only of the membrane 31 and the capsule 71.

Alternatively, the membrane may be non-removably attached to the housing 30. In this case, at the end of the deposition step 300, a housing 30 integrating the membrane 31 and the lens capsule is obtained. This housing can be used subsequently to perform a culture operation.

2.4. Lyophilization

The lyophilization step 400 dehydrates (i.e., removes the water contained therein) the lens capsules. This lyophilization step facilitates the transport and subsequent storage of the allograft or xenograft materials (obtained at the end of the process) since they no longer have to be kept in a liquid medium.

The lyophilization step 400 can be implemented using a lyophilizer (freezing the cultured lens capsules and then evaporating the ice under vacuum without melting it, etc.), or using any other lyophilization technique known to the skilled person.

Advantageously, the lyophilization step 400 can be carried out on each assembly composed of the membrane 31 and the lens capsule (or even on each housing 30 integrating the membrane 31 and the cultured lens capsule). This limits the number of handling operations on the lens capsule, as these handling operations are likely to cause damage to the lens capsule. Alternatively, the capsule may also be lyophilized alone (but this lyophilization is complex to achieve because the capsule is fragile).

Once the lens capsule(s) has/have been lyophilized, it/they is/are subjected to a sterilization step.

2.5. Sterilization

The sterilization step 500 reduces the number of microorganisms that may be attached to the lyophilized lens capsule(s). The sterilization step 500 further increases the shelf life of the lyophilized lens capsule(s).

The sterilization step 500 may be implemented by any sterilization technique known to the skilled person such as irradiation (for example subjecting each lyophilized lens capsule to electron beam radiation, gamma radiation, or ultraviolet light) for a certain period of time.

Advantageously, the sterilization step 500 can be implemented on each housing 30 integrating the membrane 31 and the lyophilized lens capsule.

Alternatively, the sterilization step 500 may be performed on the assembly consisting of the membrane 31 and the lyophilized lens capsule. In this case, if the lyophilizing step 400 has been performed on the housing 30 incorporating the membrane 31 and the lens capsule, the assembly consisting of the membrane 31 and the lyophilized lens capsule may be removed from the housing 30 prior to the implementation of the sterilization step 500.

Alternatively, the sterilization step 500 can be performed only on the lyophilized lens capsule, which can be easily detached from the membrane 31 after lyophilization.

2.6. Packaging

At the end of the sterilization step 500, either the sterilized lens capsule alone, or the stack composed of the membrane 31 and the sterilized lens capsule, or the housing 30 integrating the membrane 31 and the sterilized lens capsule is packaged in a package allowing the storage and transport of the allograft or xenograft materials obtained.

3. Use of Grafting Materials

To perform a transplant, the practitioner receives the package containing the allograft or xenograft materials.

Once the material is removed from its packaging, it must be rehydrated.

To do this, the practitioner can rehydrate the lyophilized and sterilized lens capsule either:

- directly in its housing (if it has been packaged with the lens capsule), or
- on its membrane (if only the membrane and the capsule have been packaged), or
- rehydrate only the lens capsule (if it was packaged alone or was detached from the membrane before the rehydration operation).

Rehydration 610 of the lens capsule may be achieved using water, or saline or ophthalmologic surgical intraocular perfusion fluid or any other fluid known to the skilled person.

Once the allograft or xenograft material is rehydrated, the grafting procedure can be implemented in the conventional manner.

3.1. Grafting a Decellularized Capsule

In certain applications, the unpackaged lens capsule can be grafted 620 directly after rehydration 610.

For example, the decellularized and rehydrated capsule can be grafted behind a cornea affected by Fuchs' dystrophy and from which the surgeon has previously removed Descemet's membrane. The capsule thus grafted makes it possible to guide the in vivo regrowth of endothelial cells.

Alternatively, the decellularized and rehydrated capsule can be grafted to plug a macular hole. In this case, the grafted capsule helps to promote healing (the capsule plays the same healing role as the flaps of internal limiting membrane that the surgeon can put in the macular hole to promote its healing).

Of course, the decellularized and rehydrated lens capsule graft can be used for any other application known to the skilled person.

3.2. Grafting a Cell-Covered Capsule

For other applications, the rehydrated lens capsule can be grafted 640 after the implementation of a culture step 630: in vitro cell culture on the surface of each decellularized/lyophilized/sterilized/rehydrated lens capsule to obtain cultured lens capsules; by way of non-limiting examples:

- corneal endothelial cells for corneal endothelial reconstructions (called tissue engineered endothelial keratoplasty, or TEEK),
- corneal epithelial cells for ocular surface reconstructions,
- cells of the pigmented epithelium of the retina for diseases such as certain retinitis pigmentosa specifically affecting this layer or for common diseases such as age-related macular degeneration (AMD),
- photoreceptor (cone and/or rod) for retinitis pigmentosa,
- ganglion cells for optic neuropathies.

The step of culture by the target cells (corneal, retinal, etc.) 630 of the rehydrated lens capsules (decellularized from their own cells) provides cultured lens capsules that can be grafted on a patient (bioengineering).

Figure 9:
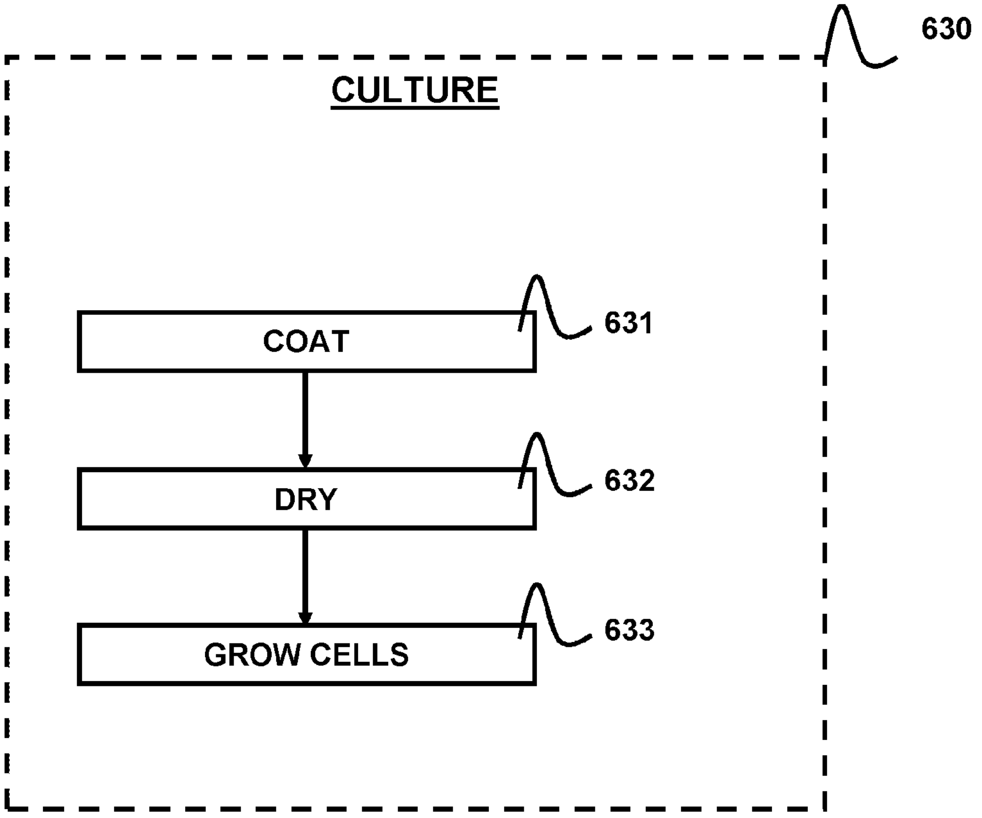
FIG. 9 is a schematic representation of the substeps for culturing a lens capsule prepared by the preparation process according to the invention.

As illustrated in FIG. 9, the culturing step 630 may comprise a substep of coating 631 the lens capsule with a substance that promotes adhesion of the target cells/tissues to be cultured on the decellularized lens capsule—such as a substance composed of fibronectin, laminin, proteoglycans) or any other substance known to the skilled person.

This coating substep 631 may be followed (if necessary) by a drying substep 632 prior to cell or tissue culture.

Finally, the culturing step 630 comprises a substep of growing cells/tissues 633 on the decellularized lens capsule:

- the reservoir 10 of the culture device is filled with culture liquid,
- the removable tray 20 is installed on the reservoir 10, and
- each housing 30 is installed inside a respective circular hole 21.

Once the culture has been performed, the material obtained can be used to perform a graft.

4. Tests

The following test was performed by the inventors to demonstrate the possibility of cell culture on a decellularized lens capsule.

4.1. Objective

The objective is to seed corneal endothelial cells (hereinafter CECs) on a lens capsule in order to evaluate the advantage of its use as a biological support for the bioengineering of an endothelial graft.

4.2. Materials

Lens capsules of 6 millimeters in diameter (surgical waste from cataract surgery patients with femtosecond laser cutting of the capsule) were used. These lens capsules were decellularized, sterilized and stored in pure water at 4° C. before use.

CECs in primary culture at 5th passage were used.

4.3. Endothelialization

The 6-mm-diameter lens capsules were deposited on Nunc culture insert membranes on a 24-well plate. The polycarbonate membrane was microperforated and had a pore size of 0.4 mm. The adhesion of the capsule to the membrane was obtained by simple drying. The capsules on the insert membranes were lyophilized and then stored at room temperature in an airtight box.

On the day of use for cellularization, the capsule was rehydrated by immersing the culture insert in a well containing phosphate-buffered saline.

A coating medium was added (laminin LMN511). The cells were seeded at 5000 cells/mm$^2$.

Seven days after the start of in vitro culture of the lens capsules in the CEC solution, the CEC membranes were visualized by transmission light microscopy after staining with alizarin red and by confocal microscopy after staining with Dioc6 (3,3'-dihexyloxacarbocyanine iodide, a fluorescent dye for membranes of intracellular organelles), which allows specific visualization of the cytoplasm, and Dapi (4',6-diamidino-2-phenylindole), which is specific to nuclei.

4.4. Results

Alizarin red staining showed total coverage of the lens capsule surface by CECs with a residual endothelial cell density (ECD) of about 3000 cells/$mm^2$.

Confocal microscopy confirmed the formation of a cell monolayer uniformly covering the surface of the lens capsule The lens capsule allowed a CEC cell monolayer to be formed on its surface while maintaining excellent transparency and strength.

Experimental endothelial grafts were performed in rabbits using a TEEK composed of a human lens capsule treated as described above and endothelialized with human CECs.

On the day of transplantation, the removable part of the cell culture insert with a thin plastic ring and the polycarbonate membrane to which the endothelialized lens capsule adheres was sterilely grasped by hand. The TEEK can thus be handled without any trauma. The face of the polycarbonate membrane was dried with a surgical microsponge. Three asymmetrical markings were made on the edge of the TEEK (clearly visible by transparency to the naked eye) and via its back face through the polycarbonate membrane in order to identify the direction (endothelialized face versus cell-free face) during grafting in the recipient eye.

The TEEK was then stained with 0.4% trypan blue (following the same protocol as in a usual endothelial graft) directly into the culture insert. The dye was applied to both sides of the membrane to thoroughly permeate the graft by both faces.

The polycarbonate membrane has been detached from its plastic ring with a scalpel blade or a drill bit of larger diameter than the TEEK. The TEEK can thus be handled without any contact since only the membrane is held with the surgeon's forceps.

The membrane+TEEK assembly was immersed in a usual surgical irrigation fluid of the balanced salt solution (BSS) type. The TEEK was detached from the membrane using a spatula to lift the edge of the TEEK. The blue staining of the TEEK helps to visualize it well during this phase performed under the operating microscope (the TEEK can be recolored with trypan blue if the surgeon deems it necessary).

The TEEK rolled up on itself to form a roll with the CECs on the outside, similar to a natural Descemet Membrane Endothelial Keratoplasty (DMEK) donor graft.

The TEEK was handled as a DMEK graft, inserted into a glass injector or plastic injection cartridge, and injected into the recipient eye according to standard surgical procedure.

It was performed in the eye by usual surgical maneuvers. The correct orientation (endothelialized face directed towards the interior of the eye and cell-free face against the cornea) was verified by the asymmetric colored marks and/or the three notches and/or three jaws present at the periphery of the TEEK.

The TEEK was held in place by a gas bubble (air or a mixture of 80% air and 20% SF6 (sulfur hexafluoride) gas) as in human endothelial transplantation.

The good functioning of the TEEK was then confirmed by its capacity to maintain fine and transparent for 4 weeks the cornea of the rabbit previously made pathological by destruction of its own CEC.

Control rabbits grafted with a capsule but WITHOUT cellularization by CECs served as a control, their corneas did not improve and remained edematous.

5. Conclusions

The preparation process described above provides an allograft or xenograft material from a lens capsule.

The decellularized lens capsule is a non-immunogenic tissue, and by definition biocompatible. It is also transparent and constitutes an excellent support for cell culture.

The human origin guarantees easier acceptance by the health authorities. It is possible to secure the donation by a serological diagnosis of the donors (such a diagnosis is already compulsory for corneal donations; it will be easy to obtain for cataract surgeons).

The main use of the grafts obtained by implementing the process according to the invention concerns the treatment of ocular pathologies. These grafts can be:

- endothelial grafts; the grafts obtained using the process according to the invention faithfully reproduce the grafts prepared from donor corneas of the Descemet Membrane Endothelial Keratoplasty (DMEK) or tissue engineered endothelial keratoplasty (TEEK) type: they do not change surgical habits and their number is not limited,
- other grafts (epithelial, conjunctival, retinal) to bring stem or differentiated cells on a transparent, easy-to-handle support,
- guiding grafts ("descemetic dressing" to treat endothelial dysfunction by guiding healing) or healing grafts (healing of macular holes).

The reader will appreciate that the deposition of the received lens capsules on a membrane of a respective housing individually facilitates the entire processing chain of the lens capsule from its decellularization to its rehydration for transplantation. Indeed, the use of a housing integrating a support membrane on which the lens capsule is deposited limits the risks of deterioration of the lens capsule (by limiting the direct contacts of the lens capsule by the various operators).

The reader will have understood that many modifications can be made to the previously described invention without materially departing from the new teachings and advantages described herein.

For example, the process may comprise a step of marking the capsules to indicate an orientation, either by mechanical cutting (drill bit or laser) or by marking with biocompatible ink with an asymmetrical sign, making it possible to differentiate the two faces of the lens capsule (in particular when one of the faces carries cells, the latter being the one that is to be brought into contact with the diseased recipient cornea).

The invention claimed is:

1. A method for preparing an allograft or xenograft material from a lens capsule consisting essentially of:

a) decellularizing a lens capsule to obtain a decellularized lens capsule, b) depositing the decellularized lens capsule on a microporous support membrane having a pore size of 0.4 mm to obtain a stack consisting essentially of the decellularized lens capsule and the microporous support membrane, c) lyophilizing the stack to obtain a lyophilized stack, d) marking the decellularized lens capsule to form orientation markers, said marking step consisting of applying a biocompatible ink through the microporous support membrane, e) sterilizing the lyophilized stack to obtain a sterilized stack, and f) packaging the sterilized stack to obtain the allograft or xenograft material.

2. The method as claimed in claim 1, wherein after step f) the lens capsule is cut to form a gripping means.

3. The method as claimed in claim 1, wherein, prior to step a):

a primary biological material selected from the group consisting of a globe and a cornea from an organ donation, a lens capsule from a cataract operation and constituting surgical waste is introduced, and a step of extracting the lens, and then a step of cutting anterior and posterior lens capsules.

4. The method as claimed in claim 3, wherein the step of cutting the anterior and posterior lens capsules consists essentially of:

inserting the lens in its entirety into a holding device consisting essentially of a housing transparent for laser radiation, and suction means for pressing the lens into the housing, then cutting an anterior face of the lens capsule using laser radiation to obtain a cut anterior disk, then cutting a posterior face of the lens capsule using laser radiation to obtain a cut posterior disk, and finally dissecting the cut anterior and posterior disks to obtain the anterior and the posterior lens capsule.

5. The method as claimed in claim 1, further consisting essentially of a step of marking the lens capsule to form orientation marker means, said marking step consisting of applying a biocompatible ink through the microporous support membrane.

6. The method as claimed in claim 1, wherein the decellularization step consists essentially of immersing the lens capsule in a decellularizing liquid, and rinsing the lens capsule with a rinsing liquid.

7. The method as claimed in claim 1, wherein the deposition step consists essentially of positioning the lens capsule flat on the microporous support membrane, and desiccating the lens capsule to promote adhesion of the lens capsule to the microporous support membrane.

8. The method as claimed in claim 1, further consisting essentially of, after the packaging step, a cell or tissue culture step, said culture step including the substeps consisting of:

g) coating the lens capsule with a substance that promotes adhesion of cells/tissues to be cultured, and h) growing the cells/tissues on the lens capsule.

9. The method as claimed in claim 1, further consisting essentially of, after the packaging step, a step of rehydrating the allograft or xenograft material, to allow use of the lens capsule either directly as a healing agent, or after implementation of a cell or tissue culture step.

10. The method as claimed in claim 9, wherein the decellularization step consists essentially of immersing the lens capsule in a decellularizing liquid, and rinsing the lens capsule with a rinsing liquid.

11. The method as claimed in claim 10, wherein the deposition step consists essentially of positioning the lens capsule flat on the microporous support membrane, and desiccating the lens capsule to promote adhesion of the lens capsule to the microporous support membrane.

12. The method as claimed in claim 10, wherein the method further consists essentially of, after the packaging step, a cell or tissue culture step, said culture step consisting of coating the lens capsule with a substance that promotes adhesion of cells/tissues to be cultured, and growing the cells/tissues on the lens capsule.

13. The method as claimed in claim 10, wherein the preparation process further consists essentially of, after the packaging step, a step of rehydrating the allograft or xenograft material, to allow use of the lens capsule either directly as a healing agent, or after implementation of a cell or tissue culture step.

* * * * *